US011998219B2

(12) United States Patent
Anderson

(10) Patent No.: US 11,998,219 B2
(45) Date of Patent: *Jun. 4, 2024

(54) SURGICAL SAW BLADE FOR WEDGE OSTEOTOMIES

(71) Applicant: CORTICAL EDGE ORTHOPEDICS LLC, Hayward, WI (US)

(72) Inventor: Keith Richard Anderson, Hayward, WI (US)

(73) Assignee: Cortical Edge Orthopedics LLC, Hayward, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/873,956

(22) Filed: Jul. 26, 2022

(65) Prior Publication Data

US 2023/0081365 A1 Mar. 16, 2023

Related U.S. Application Data

(63) Continuation of application No. 16/734,793, filed on Jan. 6, 2020, now Pat. No. 11,395,663, which is a continuation of application No. 14/605,634, filed on Jan. 26, 2015, now Pat. No. 10,524,803, which is a continuation of application No. 12/732,398, filed on Mar. 26, 2010, now Pat. No. 8,939,981.

(60) Provisional application No. 61/164,594, filed on Mar. 30, 2009.

(51) Int. Cl.
*A61B 17/14* (2006.01)

(52) U.S. Cl.
CPC ............ *A61B 17/142* (2016.11); *A61B 17/14* (2013.01)

(58) Field of Classification Search
CPC ..... A61B 17/14; A61B 17/142; A61B 17/144; A61B 17/147; A61B 17/149
See application file for complete search history.

(56) References Cited

U.S. PATENT DOCUMENTS 5,749,875 A * 5/1998 Puddu .................... A61B 17/88
606/915
2007/0233131 A1* 10/2007 Song .................. A61B 17/1671
606/79

* cited by examiner

*Primary Examiner* — Si Ming Ku
(74) *Attorney, Agent, or Firm* — Garvey, Smith & Nehrbass, Patent Attorneys, L.L.C.; Julia M. FitzPatrick; Gregory C. Smith

(57) ABSTRACT

A surgical blade having an attachment base positioned at a proximal end and a wedge-shaped blade. The wedge-shaped blade includes a cutting tip having a first plurality of cutting teeth, which define a cutting edge along the distal end for starting an osteotomy. The wedge-shaped blade includes a second plurality of teeth positioned along rows. Each row is positioned at offset planes from adjacent rows along the wedge-shaped blade.

16 Claims, 3 Drawing Sheets

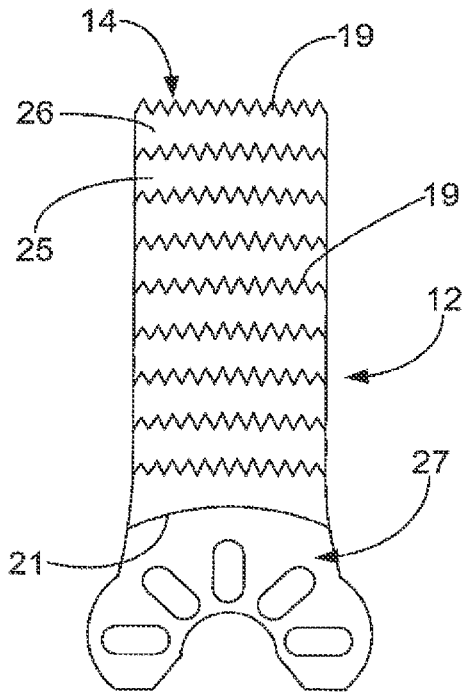
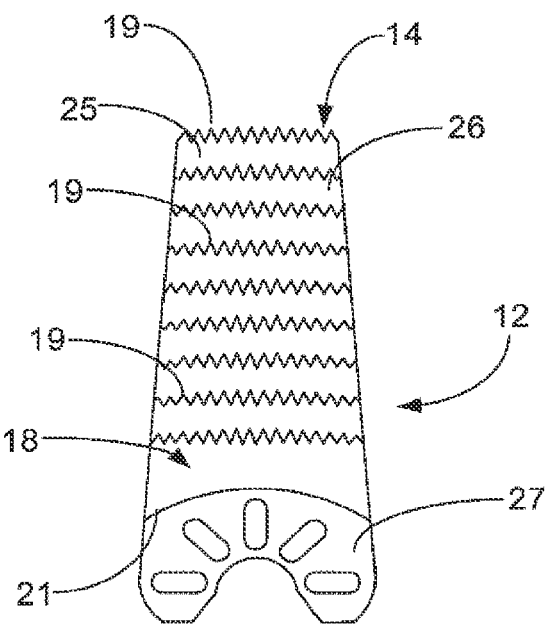
FIG. 4 FIG. 7
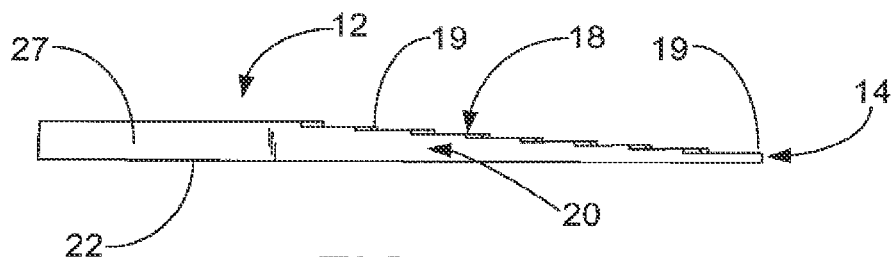
FIG. 5
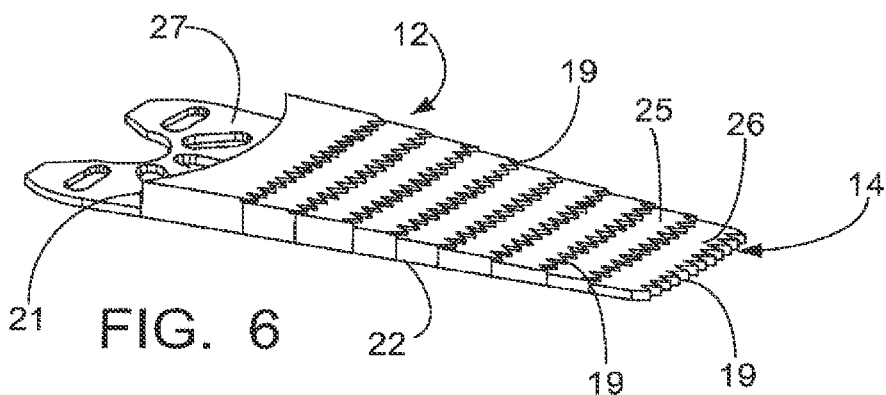
FIG. 6

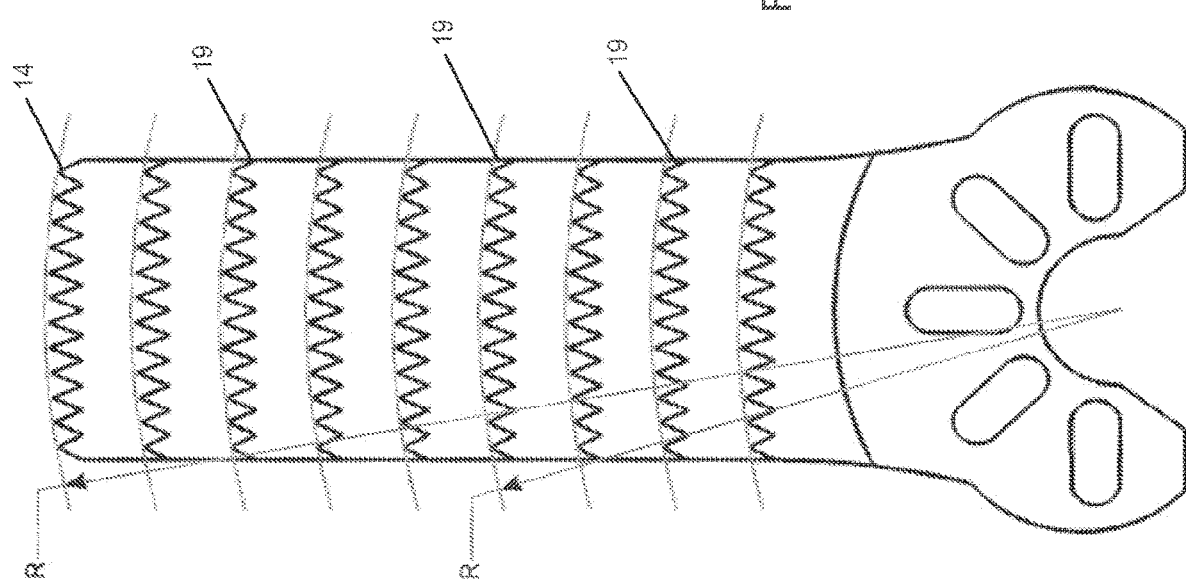

SURGICAL SAW BLADE FOR WEDGE OSTEOTOMIES

CROSS-REFERENCE TO RELATED APPLICATIONS

This application is a continuation application of U.S. patent application Ser. No. 16/734,793, filed Jan. 6, 2020, which is a continuation application of U.S. patent application Ser. No. 14/605,634, filed Jan. 26, 2015 (issued as U.S. Pat. No. 10,524,803 on Jan. 7, 2020), which is a continuation of U.S. patent application Ser. No. 12/732,398, filed Mar. 26, 2010 (issued as U.S. Pat. No. 8,939,981 on Jan. 27, 2015) which claims the benefit of U.S. Provisional Patent Application Ser. No. 61/164,594, filed Mar. 30, 2009, each of which is hereby incorporated herein by reference in its entirety.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

Field of the Invention

The present invention generally relates to surgical devices. More particularly, the present invention relates to a surgical saw blade for wedge osteotomies.

General Background of the Invention

Current surgical saw blades make straight or crescentic shaped osteotomies. This causes the user to make multiple osteotomies to resect a wedge of bone. Creation of multiple osteotomies is time consuming, and can create inconsistent wedge sizes and planar inaccuracies.

As can be seen, there is a need for a surgical saw blade for precise, reproducible, and predictable wedge osteotomies.

BRIEF SUMMARY OF THE INVENTION

The apparatus of the present invention solves the problem in a simple and straightforward manner. What is provided is a surgical blade for use with a saw, the bland which includes a cutting tip, having a plurality of cutting teeth; a shaft having a cutting slope, with the plurality of teeth positioned along multiple planes on the cutting slope; a neck portion; and a saw base; wherein the saw causes the blade to oscillate as it undergoes the cutting procedure.

These and other features, aspects and advantages of the present invention will become better understood with reference to the following drawings, description and claims.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 4 illustrates a top view of a second embodiment of the invention;

FIG. 5 illustrates a side view of a second embodiment of the invention;

FIG. 6 illustrates an overall view of a third embodiment of the invention;

FIG. 7 illustrates a top view of a third embodiment of the invention; and

FIG. 8 illustrates a top view of an embodiment of the invention and shows the rows of cutting teeth and cutting tip having a radius.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

An embodiment of the present invention adds a slope on one side of the blade from the distal tip to the proximal shaft with teeth to allow for a precise predetermined wedge of bone to be resected with performing only one osteotomy. The present invention relates to a surgical saw blade for precise, reproducible, and predictable wedge osteotomies.

Embodiments of the present invention include a surgical saw blade for creating precise wedge osteotomies that are reproducible and predictable, to be used to correct angular deformities in bones and joints. An embodiment of the invention, which may be called a "wedge osteotomy blade," creates a precise predetermined wedge cut in bone with one pass. This can eliminate the need for two passes with a standard bone saw blade, as well as eliminate planar inconsistencies associated with multiple passes. The osteotomy is reproducible and predictable.

Figure 1:
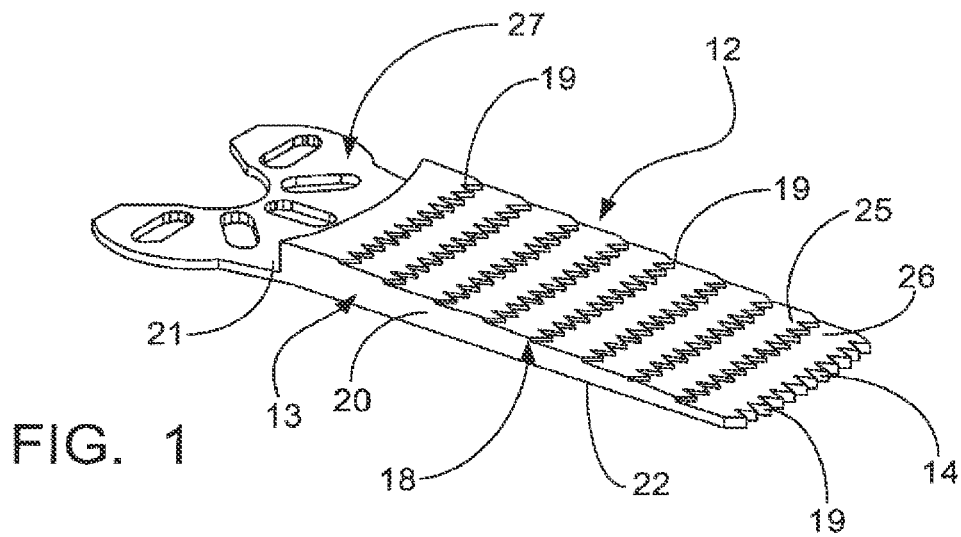
FIG. 1 illustrates an overall view of a first embodiment of the invention.
Figure 2:
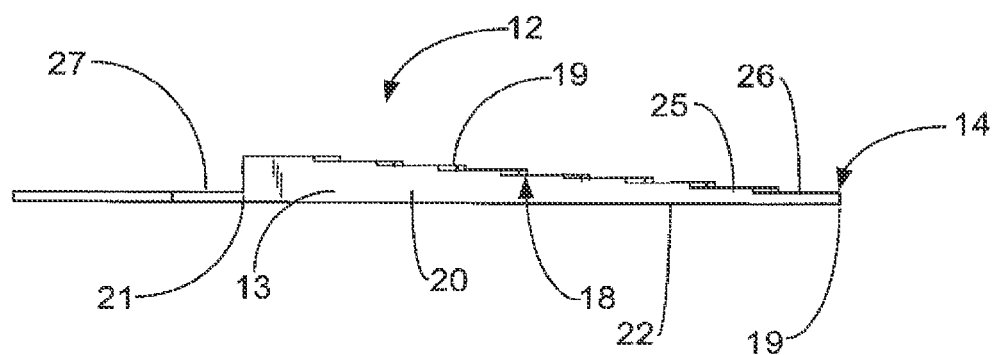
FIG. 2 illustrates a side view of a first embodiment of the invention.
Figure 3:
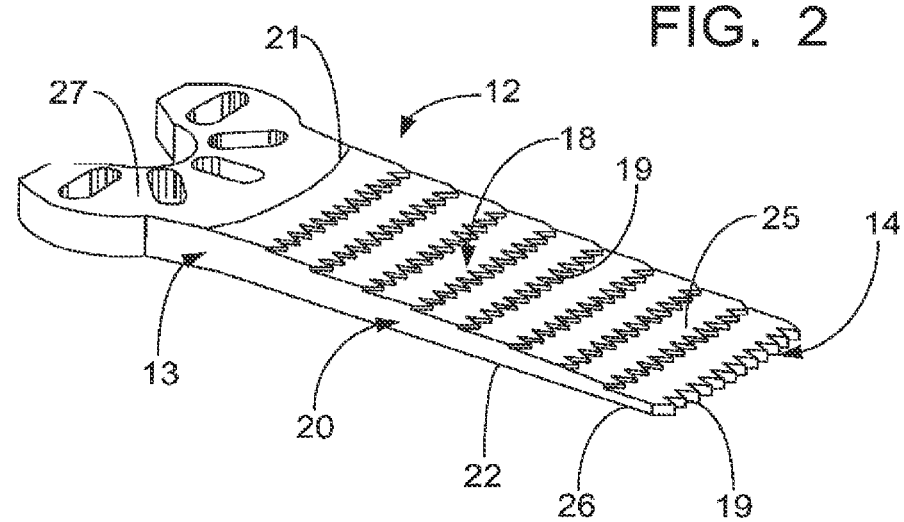
FIG. 3 illustrates an overall view of a second embodiment of the invention.

FIGS. 1 through 8 illustrate the preferred embodiments of the device of the present invention. Broadly, each embodiment of the present invention, as illustrated in FIGS. 1 through 8, is generally a surgical saw blade 12 for precise, reproducible, and predictable wedge osteotomies. Although each embodiment has slight modifications over other embodiments, it should be known that the principal inventive features as claimed are found in each embodiment as shown in the FIGS. 1 through 8.

In each embodiment, the wedge osteotomy blade 12 is a device designed to create a precise, predetermined wedge osteotomy in bone. The wedge osteotomy blade 12 could be retro-fitted to any surgical saw configuration. The wedge osteotomy blade 12 could be constructed of surgical grade stainless steel or any other material used for cutting bone that can be sterilized.

The blade 12 further comprises a blade body 13 having a cutting tip 14 which is designed with multiple teeth 19 to create a cut in bone when oscillated. This tip 14 preferably has a radius, and could contain any number of teeth. The radius R is illustrated in FIG. 8. The teeth could be any length or of any design.

There is provided a cutting slope 18 designed on one side 21 of a shaft 20, with the underside 22 being flat. The cutting slope 18 could be any rise over run desired for creating a wedge osteotomy. The slope should be at its highest height near the neck 21 and at its lowest height at the cutting tip 14.

The cutting slope 18 has multiple rows of cutting teeth 19. Each row of teeth 19 is elevated above the run of the distal row of teeth 19. The cutting teeth 19 could be of any design and preferably have the same radius, number of teeth, and same length as the cutting tip 14.

The shaft 20 is designed to be flat on four surfaces and accommodates the cutting slope 18 on the fifth surface 25, and the cutting tip 14 on the sixth surface 26. The shaft 20 could be of any shape, preferably rectangular or trapezoidal. The shaft 20 extends from the neck 21 to the cutting tip 14. The shaft 20 could be any length and width.

The neck 21 is designed to be the transition from the shaft 20 to the saw attachment base 27.

The saw attachment base 27 allows the blade 12 to be attached to a surgical saw (not illustrated).

The invention provides the surgeon a way to make accurate wedge osteotomies with predictability and reproducibility. The wedge osteotomy blade 12 has a cutting tip 14 to start the osteotomy. The cutting slope 18 resects bone as it enters, leaving a wedge osteotomy. The cutting slope 18 has rows of cutting teeth 19 for resection of bone while oscillating. The shaft 20 is of a predetermined length and width and supports the cutting slope 18. The neck 21 is the transition of the shaft 20 into the saw attachment base 27. The saw attachment base 27 can be of any design to fit any number of surgical saw manufacturers.

The wedge osteotomy blade 12 is one component. It can be manufactured from surgical grade stainless steel or any other material used for cutting bone that can be sterilized.

The wedge osteotomy blade 12 works by creating a precise, predetermined, wedge osteotomy in bone. To perform an osteotomy with the wedge osteotomy blade 12, the Surgeon has to first attach the blade 12 to a surgical saw (not illustrated). The surgical saw could be from any manufacturer. The wedge osteotomy blade 12 which is being oscillated by the surgical saw is then introduced into the bone in a straight fashion. The surgeon can dictate whether to make a complete through and through osteotomy, or leave the distal cortex intact as a hinge. After satisfactory wedge resection, saw is disengaged and removed from bone. It leaves a precise, predetermined, wedge osteotomy for the surgeon to correct angular deformities in bones and joints.

To make this invention a detailed drawing, or a computer aided design drawing is needed. With the aforementioned drawings, one could machine a wedge osteotomy blade from surgical grade stainless steel or any other material used for cutting bone that can be sterilized.

Another way to reconfigure the wedge osteotomy blade 12 would be to have the cutting slope 18 on two opposite sides of the shaft 20 to create a two sided cutting surface for a "V" type wedge resection, instead of the "right triangle" shaped wedge.

A person would use the invention in the following way. First the saw attachment base 27 is attached to a surgical saw from any number of manufactures. The next step would be to turn the surgical saw on, which in turn would oscillate the wedge osteotomy blade 12. The surgeon then engages the bone with the cutting tip 14 first. As the surgeon advances the blade 12 in a linear fashion through the bone the cutting slope 18 resects a wedge of bone with precision, predictably, and reproducibility.

It should be understood, of course, that the foregoing relates to exemplary embodiments of the invention and that modifications may be made without departing from the spirit and scope of the invention as set forth in the following claims.

The following is a list of parts and materials suitable for use in the present invention.

| PARTS LIST | |
| --- | --- |
| Part Number | Description |
| 12 | wedge osteotomy blade |
| 13 | blade body |
| 14 | cutting tip |
| 18 | cutting slope |
| 19 | cutting teeth |
| 20 | shaft |
| 21 | neck |
| 22 | underside |
| 25 | fifth surface |
| 26 | sixth surface |
| 27 | saw attachment base |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A surgical blade comprising:
 a wedge-shaped blade extending between a proximal end and a distal end, the wedge-shaped blade including:
 a cutting tip having a first plurality of cutting teeth, which define a cutting edge along the distal end for starting an osteotomy,
 a second plurality of teeth positioned along rows, each row positioned at offset planes from adjacent rows along the wedge-shaped blade, and
 a surface defining the proximal end, wherein the surface is curved and does not include any teeth; and
 an attachment base that extends between a base proximal end and a base distal end, that is flat, and that includes multiple openings that are oval-shaped, wherein the base distal end adjoins the proximal end of the wedge-shaped blade.

2. The surgical blade of claim 1, further comprising a neck portion intermediate the wedge-shaped blade and the attachment base.

3. The surgical blade of claim 1, wherein the wedge-shaped blade includes a cutting slope along which the second plurality of teeth is positioned with each row of teeth elevated above the cutting tip.

4. The surgical blade of claim 1, wherein the wedge-shaped blade comprises steel.

5. The surgical blade of claim 1, wherein the wedge-shaped blade comprises stainless steel.

6. The surgical blade of claim 1, wherein the wedge-shaped blade does not include teeth on at least three of its sides.

7. The surgical blade of claim 1, wherein the wedge-shaped blade is flat on four sides and accommodates the second plurality of teeth on a fifth side and the cutting tip on a sixth side.

8. The surgical blade of claim 1, wherein the wedge-shaped blade includes a bottom plane, wherein the offset planes are parallel to the bottom plane.

9. The surgical blade of claim 1, wherein the rows include eight rows.

10. The surgical blade of claim 1, wherein the first plurality of teeth and the second plurality of teeth include triangle-shaped teeth.

11. The surgical blade of claim 1, wherein the first plurality of teeth and the second plurality of teeth decrease in width as said teeth extend towards the distal end.

12. The surgical blade of claim 1, wherein the first plurality of teeth and the second plurality of teeth have tips that are positioned along a radius.

13. The surgical blade of claim 1, wherein each row of the second plurality of teeth is positioned along a different radius than adjacent rows.

14. The surgical blade of claim 1, wherein each row includes twelve teeth.

15. The surgical blade of claim 1, wherein the wedge-shaped blade includes a cutting slope along which the rows are positioned.

16. The surgical blade of claim 15, wherein the cutting slope is a linear slope.

\* \* \* \* \*